(12) United States Patent
Liu et al.

(10) Patent No.: US 10,682,488 B2
(45) Date of Patent: Jun. 16, 2020

(54) HUMIDIFICATION DEVICE, HUMIDIFIER AND VENTILATOR

(71) Applicant: BMC MEDICAL CO., LTD., Beijing (CN)

(72) Inventors: Lijun Liu, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 373 days.

(21) Appl. No.: 15/542,438

(22) PCT Filed: Dec. 31, 2015

(86) PCT No.: PCT/CN2015/100054
§ 371 (c)(1),
(2) Date: Jul. 9, 2017

(87) PCT Pub. No.: WO2016/110218
PCT Pub. Date: Jul. 14, 2016

(65) Prior Publication Data
US 2018/0001050 A1    Jan. 4, 2018

(30) Foreign Application Priority Data

Jan. 9, 2015    (CN) .......................... 2015 1 0011619

(51) Int. Cl.
*A61M 16/16*    (2006.01)
*A61M 11/04*    (2006.01)
*A61M 16/10*    (2006.01)

(52) U.S. Cl.
CPC ......... *A61M 16/162* (2013.01); *A61M 11/042* (2014.02); *A61M 16/109* (2014.02); *A61M 2205/21* (2013.01)

(58) Field of Classification Search
CPC .. A61M 16/109; A61M 16/145; A61M 16/16; A61M 16/161; A61M 16/162;
(Continued)

(56) References Cited

U.S. PATENT DOCUMENTS

| 4,993,411 A | 2/1991 | Callaway |
| 5,329,939 A | 7/1994 | Howe |

(Continued)

FOREIGN PATENT DOCUMENTS

| CN | 102711892 A | 10/2012 |
| CN | 103429293 A | 12/2013 |

(Continued)

*Primary Examiner* — Annette Dixon
(74) *Attorney, Agent, or Firm* — Bayramoglu Law Offices LLC (57) ABSTRACT

The present disclosure discloses a humidification device, a humidifier and a ventilator, overcoming the deficiency that when the structure of a water tank of a current ventilator causes the water tank to tilt or sway, it is easy for a large amount of water to enter a heating portion. The humidification device comprises a heating portion and a liquid inlet structure adding liquid to the heating portion. The heating portion comprises an accommodating chamber and a transition chamber limiting the amount of liquid in the accommodating chamber, and the liquid inlet structure is communicated with the transition chamber and allows the liquid to enter the transition chamber. According to embodiments of the present disclosure, a large amount of stored water may be prevented from entering the heating portion and thus affecting the heating efficiency when a water tank or a similar humidification device tilts.

13 Claims, 10 Drawing Sheets

(58) Field of Classification Search
CPC .............. A61M 16/164; A61M 16/167; A61M
2205/3368; A61M 2206/14; A61M 16/08;
A61M 16/0841; A61M 16/1075; A61M
16/1085; A61M 16/1095; A61M
2005/1623; Y10S 261/65
See application file for complete search history.

(56) References Cited

U.S. PATENT DOCUMENTS

| | | | |
|---|---|---|---|
| 6,031,968 A | | 2/2000 | Holtmann |
| 6,394,084 B1* | | 5/2002 | Nitta .................... A61M 16/16 |
| | | | 128/201.13 |
| 6,997,183 B2* | | 2/2006 | Koch .................. A61M 16/161 |
| | | | 128/203.16 |
| 9,446,215 B2* | | 9/2016 | Steg ..................... A61M 16/16 |
| 2004/0221843 A1 | | 11/2004 | Baecke |
| 2005/0284475 A1 | | 12/2005 | Loescher |
| 2007/0240767 A1 | | 10/2007 | Rustad |
| 2008/0054500 A1* | | 3/2008 | Bradley .............. A61M 16/167 |
| | | | 261/70 |
| 2008/0149101 A1 | | 6/2008 | Becker et al. |
| 2013/0300005 A1 | | 11/2013 | Hou |

FOREIGN PATENT DOCUMENTS

| | | |
|---|---|---|
| CN | 104548307 A | 4/2015 |
| CN | 204446898 U | 7/2015 |
| DE | 3707228 A1 | 9/1987 |
| DE | 3627351 A1 | 2/1988 |
| DE | 102009011137 A1 | 9/2010 |
| EP | 2319568 A2 | 5/2011 |
| GB | 1509011 A | 4/1978 |
| WO | 2011086436 A1 | 7/2011 |

* cited by examiner

HUMIDIFICATION DEVICE, HUMIDIFIER AND VENTILATOR

CROSS-REFERENCE TO RELATED APPLICATION

This application is the national phase entry of International Application No. PCT/CN2015/100054, filed on Dec. 31, 2015, which is based upon and claims priority to Chinese Patent Application No. CN201510011619.7, filed on Jan. 9, 2015, the entire contents of which are incorporated herein by reference.

TECHNICAL FIELD

The present disclosure relates to a respiratory therapy device, and more particularly, to a humidification device, a humidifier and a ventilator.

BACKGROUND OF THE INVENTION

As an important constituent part of a household ventilator, a humidifier is used for effectively improving the comfort when a patient uses the ventilator. Heated humid airflow not only can reduce the side effects (such as nasal obstruction, bleeding and the like) caused by mycteroxerosis, but also can, more importantly, reduce an internal resistance of a nasal cavity, thereby effectively guaranteeing the stability of a pressure inside a face mask and improving the treatment effect and the adaptability, which is important to the patient who wears the ventilator for treatment for a long time.

Currently, for a water tank in some humidifiers in the market, a heating portion is housed in a liquid storage portion and both are sealed and separated; and then the two portions communicate each other via a communicating pore. As a water level in the heating portion drops, the liquid storage portion continuously supplements water to the heating portion.

However, when the water tank tilts at a certain angle or shakes, a large amount of water enters the heating portion from the liquid storage portion. Shortcomings such as lower heating efficiency and longer heating time may be caused by sudden increase of water in the heating portion. Moreover, when the quantity of water in the heating portion is excessive, moisture contained in the humid airflow is also excessive, and even water may be directly brought by air into the nasal cavity of the patient via a pipeline, which may cause nasal discomfort of the patient or symptoms such water choking or nasosinusitis.

SUMMARY OF THE INVENTION

A technical problem to be solved by the present disclosure is overcome the deficiency that when the structure of a water tank of a current ventilator causes the water tank to tilt or sway, it is easy for a large amount of water to enter a heating portion.

To solve the above technical problem, embodiments of the present disclosure first provide a humidification device, which comprises a heating portion and a liquid inlet structure adding liquid to the heating portion. The heating portion comprises an accommodating chamber and a transition chamber limiting the amount of liquid in the accommodating chamber, and the liquid inlet structure is communicated with the transition chamber and allows the liquid to enter the transition chamber.

Preferably, the liquid inlet structure comprises a liquid inlet pipeline, the liquid inlet pipeline stretches into the transition chamber, and a reserved interval is provided between an opening of the liquid inlet pipeline and a bottom of the transition chamber.

Preferably, a communicating pore is provided between the transition chamber and the accommodating chamber, and a sectional area of the communicating pore is smaller than that of the opening of the liquid inlet pipeline.

Preferably, the communicating pore is different, in orientation, from the opening of the liquid inlet pipeline.

Preferably, a top of the transition chamber is provided with a top cover or a wall of the transition chamber extends to a top of the heating portion.

Preferably, a bottom surface of the transition chamber is lower than that of the accommodating chamber, and the opening of the liquid inlet pipeline is lower than the bottom surface of the accommodating chamber.

Preferably, a volume of the transition chamber is smaller than that of the accommodating chamber.

Preferably, the humidification device further comprises a liquid storage portion connected with the liquid inlet structure, and the liquid storage portion is configured to store liquid entering the transition chamber through the liquid inlet structure.

The embodiments of the present disclosure further provide a humidifier, comprising a heating element and the humidification device as mentioned above, wherein the heating element heats liquid in the heating portion. The embodiments of the present disclosure further provide a ventilator, comprising a main machine and the above-mentioned humidifier connected with the main machine.

Compared with the prior art, in the embodiments of the present disclosure, a transition chamber is arranged in the heating portion, and the amount of liquid entering the accommodating chamber is limited by way of the transition chamber. In this way, a large amount of stored water may be prevented from entering the heating portion and thus affecting the heating efficiency when a water tank or a similar humidification device tilts.

According to the embodiments of the present disclosure, a phenomenon that the liquid directly enters a nasal cavity of a patient via a pipeline and thus causing discomfort of the patient when the device tilts may be prevented.

Additional characteristics and advantages of the present disclosure will be set forth in the subsequent description, and in part will be apparent from the description, or may be learned by implementing the technical solutions of the present disclosure. The objectives and other advantages of the present disclosure will be implemented and obtained by means of structures and/or procedures particularly pointed out in the description, claims and accompanying drawings.

BRIEF DESCRIPTION OF THE DRAWINGS

The accompanying drawings are provided to further understand the technical solutions of the present disclosure or the prior art, and constitute a part of the description. The accompanying drawings for the embodiments of the present disclosure, together with the embodiments of the present disclosure, are provided to interpret the technical solutions of the present disclosure, rather than limiting the technical solutions of the present disclosure.

DETAILED DESCRIPTION OF THE INVENTION

Implementations of the present disclosure will be explained in detail with reference to the accompanying drawings and the embodiments, whereby it can be fully understood how to solve the technical problem by the technical means according to the present disclosure and achieve the technical effects thereof, and thus the technical solution according to the present disclosure can be implemented. It is to be noted that as long as there is no conflict, the embodiments and all the features mentioned in all the embodiments may be combined together in any manner, and the technical solutions obtained in this manner all fall within the scope of protection of the present disclosure.

Figure 1:
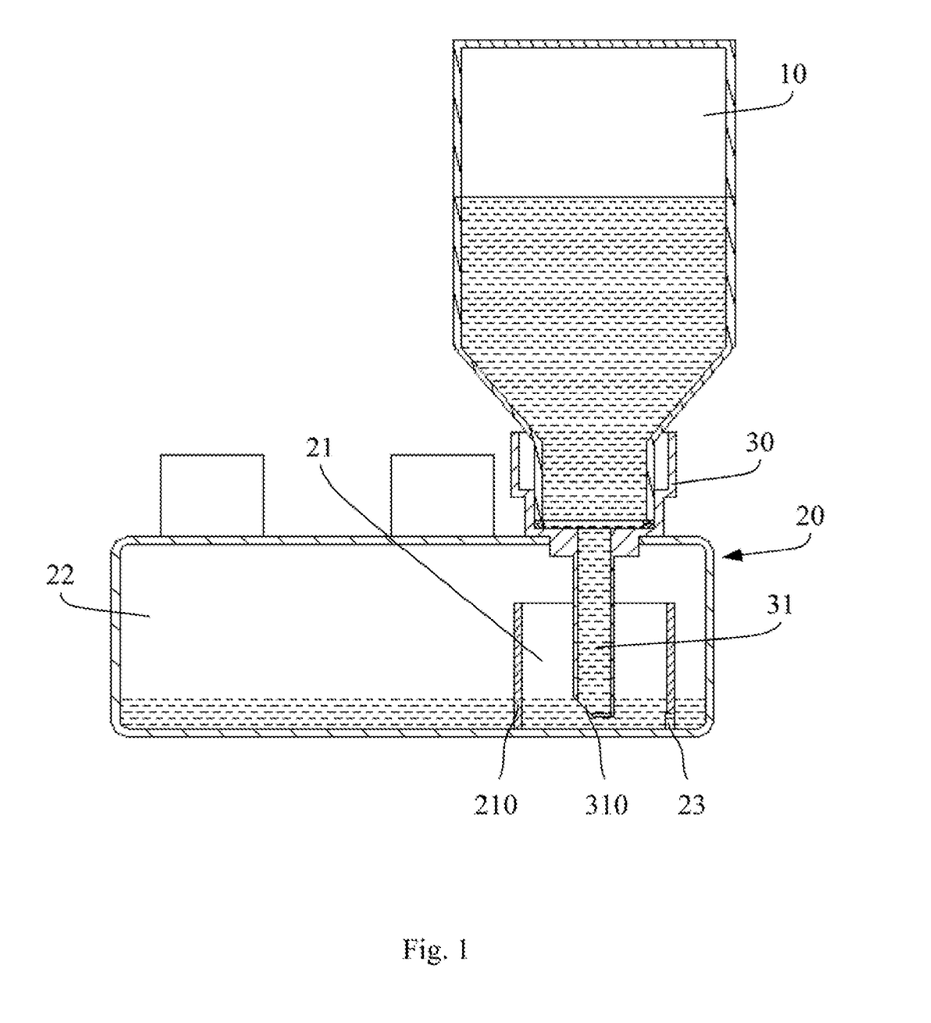
FIG. 1 is a schematic structural diagram of a humidification device according to an embodiment of the present disclosure.

As shown in FIG. 1 the humidification device according to the embodiment of the present disclosure substantially comprises a heating portion 20 and a liquid inlet structure 30 adding liquid to the heating portion 20. The heating portion 20 comprises an accommodating chamber 22 and a transition chamber 21 limiting the amount of liquid in the accommodating chamber 22. The liquid inlet structure 30 is communicated with the transition chamber 21 and allows the liquid to finally enter the transition chamber 21 via the liquid inlet structure 30.

As shown in FIG. 1, at a normal operation state, the liquid inlet structure 30 is further configured to maintain the liquid in the heating portion 20 at a preset volume. It is ensured that the liquid in the heating portion 20 may be maintained at the preset volume by limiting the liquid entering the transition chamber 21. Specifically, the liquid inlet structure 30 comprises a liquid inlet pipeline 31, wherein the liquid inlet pipeline 31 stretches into the transition chamber 21, and a reserved interval is provided between an opening 310 of the liquid inlet pipeline 31 and a bottom of the transition chamber 21. After the liquid enters the transition chamber 21 from the liquid inlet pipeline 31, the liquid in the liquid inlet pipeline 31 stops flowing into the transition chamber 21 when a liquid level of the transition chamber 21 rises above the opening 310 of the liquid inlet pipeline 31 (the liquid level of the transition chamber 21 at least is flush with the opening 310 of the liquid inlet pipeline 31). Generally, the reserved interval is greater than 5 mm and smaller than 30 mm. The reserved interval is greater than 5 mm mainly to guarantee that the liquid in the liquid inlet pipeline 31 can successfully flow out. The reserved interval is smaller than 30 mm mainly to reduce the amount of liquid in the heating portion as much as possible, so that the liquid in the heating portion evaporates more quickly under a heating condition of the same power, and thus the humidification effect is better. Furthermore, when the total amount of liquid in the heating portion is less, time spent from starting up to starting evaporation is shorter, and thus start-up efficiency is enhanced. Preferably, when the liquid is water, the reserved interval is 10 mm or 15 mm, which may provide the best humidification effect. The liquid inlet pipeline 31 may be straight or may be bent.

As shown in FIG. 1, a communicating pore 23 is provided between the transition chamber 21 and the accommodating chamber 22, which is convenient for the transition chamber 21 to intercommunicate with the accommodating chamber 22, so that the liquid in the transition chamber 21 may enter the accommodating chamber 22 via the communicating pore 23. The liquid inlet pipeline 31 is positioned in the opening 310 of the transition chamber 21, so that the liquid may be conveyed by the liquid inlet pipeline 31 into the transition chamber 21. In the embodiment of the present disclosure, a sectional area of the communicating pore 23 is smaller than that of the opening 310 of the liquid inlet pipeline 31. In this way, even though more liquid is supplemented into the transition chamber 21 via the liquid inlet pipeline 31 within a short time, not all the liquid supplemented into the transition chamber 21 via the liquid inlet pipeline 31 enters the accommodating chamber 22 because the sectional area of the communicating pore 23 is smaller than that of the opening 310 of the liquid inlet pipeline 31, which can effectively prevent the liquid in the transition chamber 21 and the liquid supplemented into the transition chamber 21 via the liquid inlet pipeline 31 from quickly entering the accommodating chamber 22. The transition chamber 21 is communicated with the accommodating chamber 22, and the sectional area of the communicating pore communicating the transition chamber 21 with the accommodating chamber 22 is smaller. Therefore, the transition chamber 21 also can effectively limit the amount of fluid entering the accommodating chamber 22.

As shown in FIG. 1, the humidification device according to the embodiment of the present disclosure may further comprise a liquid storage portion 10. The liquid storage portion 10 is connected to the liquid inlet structure 30, and may be used for storing liquid such as water or aqueous solution. The liquid stored in the liquid storage portion 10 may be added into the transition chamber 21 of the heating portion 20 via the liquid inlet structure 30. The connection between the liquid storage portion 10 and the liquid inlet structure 30 may be a detachable connection. For example, the liquid storage portion 10 is connected to the liquid inlet structure 30 by way of screw thread. In this way, after the liquid stored in the liquid storage portion 10 is used up, the liquid storage portion 10 may be detached from the liquid inlet structure 30 for replacement, or after the liquid storage portion 10 is replenished with liquid, the liquid storage portion 10 is connected again to the liquid inlet structure 30 to continue using.

The connection between the liquid storage portion 10 and the liquid inlet structure 30 is a detachable connection. The connection between the heating portion 20 and the liquid inlet structure 30 is also a detachable connection. Thus, the liquid storage portion 10 can be detached from the heating portion 20. The heating portion 20 comprises the transition chamber 21 and the accommodating chamber 22 intercommunicated. An end portion, positioned in the heating portion 20, of the liquid inlet pipeline 31 in the liquid inlet structure 30 stretches into the transition chamber 21, and the reserved interval is provided between an end portion opening 310, positioned in the transition chamber 21, of the liquid inlet pipeline 31 and the bottom of the transition chamber 21, and thus the liquid inlet pipeline 31 does not contact the transition chamber 21. The liquid flowing into the heating portion 20 via the liquid inlet structure 30 first enters the transition chamber 21 and then flows into the accommodating chamber 22.

In the embodiments of the present disclosure, a volume of the transition chamber 21 is smaller than that of the accommodating chamber 22, which is convenient to implement a function of limiting the amount of the liquid entering the accommodating chamber 22 by the transition chamber 21. It is easy to understand that when the volume of the transition chamber 21 is much smaller than that of the accommodating chamber 22, for instance, the volume of the transition chamber 21 is merely 1/5 or even 1/10 of that of the accommodating chamber 22, even though all the liquid in the transition chamber 21 enters the accommodating chamber 22 due to tilt, the amount of the liquid in the accommodating chamber 22 still is not substantially increased. Therefore, when the volume of the transition chamber 21 is smaller and the volume of the accommodating chamber 22 is larger, it may be easier to implement the function of limiting the amount of the liquid entering the accommodating chamber 22. When a bottom surface of the transition chamber 21 and that of the accommodating chamber 22 are at the same height, a sectional area of the transition chamber 21 may be smaller than that of the accommodating chamber 22, and thus the volume of the transition chamber 21 is smaller than that of the accommodating chamber 22.

When the embodiments of the present disclosure are applied, the liquid enters the transition chamber 21 via the liquid inlet pipeline 31, and simultaneously, air in the transition chamber 21 may enter the liquid storage portion 10 via the liquid inlet pipeline 31. Thus, the liquid may automatically enter the transition chamber 21 under the action of gravity. As the liquid in the accommodating chamber 22 is consumed, the liquid in the transition chamber 21 is supplemented, at any time, to the accommodating chamber 22.

At the very start (there is no liquid in the transition chamber 21 or the accommodating chamber 22), as the liquid continuously enters the transition chamber 21 and the liquid in the transition chamber 21 continuously enters the accommodating chamber 22, the liquid level of the whole heating portion 20, including the liquid level of the transition chamber 21, may rise gradually. When the liquid level of the transition chamber 21 rises above the opening 310 of the liquid inlet pipeline 31 (the liquid level of the transition chamber 21 at least is flush with the opening 310 of the liquid inlet pipeline 31), the air in the transition chamber 21 (and the accommodating chamber 22) cannot enter the liquid storage portion 10 via the liquid inlet pipeline 31 in the liquid inlet structure 30. Thus, the liquid outside cannot be supplemented to the transition chamber 21 continuously and the liquid in the heating portion 20 is maintained at a preset volume. Until the liquid in the transition chamber 21 and the accommodating chamber 22 evaporates so that the liquid level in the transition chamber 21 and the accommodating chamber 22 drops, and a gap is generated between the liquid level of the transition chamber 21 and the opening 310 of the liquid inlet pipeline 31 to allow the air to enter the liquid storage portion 10 via the liquid inlet pipeline 31 again, the liquid stored outside is continuously supplemented to the transition chamber 21 via the liquid inlet pipeline 31 under the action of gravity till the liquid in the heating portion 20 is supplemented to the preset volume again. That is, the liquid stored outside being supplemented to the heating portion 20 is a dynamic balance process.

In the embodiments of the present disclosure, the opening, positioned in the transition chamber 21, on the liquid inlet pipeline 31 may be the end portion, positioned in the transition chamber 21, of the liquid inlet pipeline 31 as shown in FIG. 1, or may be on other parts, positioned in the transition chamber 21, of the liquid inlet pipeline 31. The following embodiments of the present disclosure are described by taking the opening of the liquid inlet pipeline 31 in the transition chamber 21 being configured into the end portion (i.e. the end portion opening) of the liquid inlet pipeline 31 in the transition chamber 21 as an example.

To integrally understand the technical solutions and corresponding beneficial effects, the following embodiments of the present disclosure are described by taking a liquid storage portion being included as an example. In this way, how the stored fluid such as water is restrictively supplemented to the accommodating chamber 22 of the heating portion 20 may be completely present. However, it is to be noted that the humidification device of the present disclosure is also applicable to the technical solutions excluding the liquid storage portion for how to implement limitation on the amount of the liquid entering the accommodating chamber 22.

For ease of understanding, the embodiments of the present disclosure describe the technical solutions of the present disclosure and achievable corresponding technical effects by virtue of a common liquid, i.e. water. Those skilled in the art can understand that the technical solution of the present disclosure is also applicable to any other liquid.

When flowing into the heating portion 20 for heating, the water stored in the liquid storage portion 10 first flows into the transition chamber 21 via the liquid inlet structure 30 and then flows into the accommodating chamber 22 from the transition chamber 21.

A pipeline conveying air on which a humidity control is performed by the heating portion 20 to the patient is connected to the accommodating chamber 22. In this way, the water stored in the liquid storage portion 10 needs to flow into the transition chamber 21 via the liquid inlet structure 30 and then is supplemented to the accommodating chamber 22 in time according to a use condition of the water in the accommodating chamber 22.

In the humidification device according to the embodiments of the present disclosure, to ensure that the water in the transition chamber 21 can be supplemented to the accommodating chamber 22 in time, reduce the total amount of the water in the whole heating portion 20 as much as possible, and effectively limit the amount of the liquid entering the accommodating chamber 22 from the transition chamber 21, the communicating pore 23 communicating the transition chamber 21 with the accommodating chamber 22 may be arranged as low as possible, e.g. as close as possible to the bottom of the accommodating chamber 22, or the communicating pore 23 is directly arranged at a bottom position of the accommodating chamber 22. Typically, when the bottom surfaces of the transition chamber 21 and the accommodating chamber 22 are positioned on the same plane, the communicating pore 23 may be arranged based on this plane.

In a normal service, the water in the transition chamber 21 may be normally supplemented to the accommodating chamber 22 via the communicating pore 23, so as to maintain normal supplementation of the moisture in the whole heating portion 20 supplied to the patient and guarantee that the humidity of the air conveyed to the patient meets a requirement of the patient. To reduce a flow rate of the water flowing into the accommodating chamber 22 from the transition chamber 21 when the humidification device tilts, the sectional area of the communicating pore 23 may be as small as possible under the condition that the normal water supplementation is guaranteed, as long as it is ensured that a surface tension of the water can be overcome and the water can be allowed to flow between the transition chamber 21 and the accommodating chamber 22. In this way, even though the humidification device tilts or sways (even if tilts or sways at 90 degrees), the water in the transition chamber 21 does not enter the accommodating chamber 22 quickly and largely through the communicating pore 23. Typically, the sectional area of the communicating pore 23 may be smaller than that of the end portion opening 310 of the liquid inlet pipeline 31 in the liquid inlet structure 30.

As shown in FIG. 1, the end portion opening 310, positioned in the transition chamber 21, of the liquid inlet pipeline 31 is different, in orientation, from the communicating pore 23. Typically, the end portion opening 310, positioned in the transition chamber 21, of the liquid inlet pipeline 31 is opposite, in opening orientation, to the communicating pore 23. Thus, when the humidification device of the present disclosure is placed as shown in FIG. 1, no matter whether the orientation tilts leftward (as shown in FIG. 2) or tilts rightward (as shown in FIG. 3), the water in the transition chamber 21 does not flow into the accommodating chamber 22 limitlessly.

Figure 2:
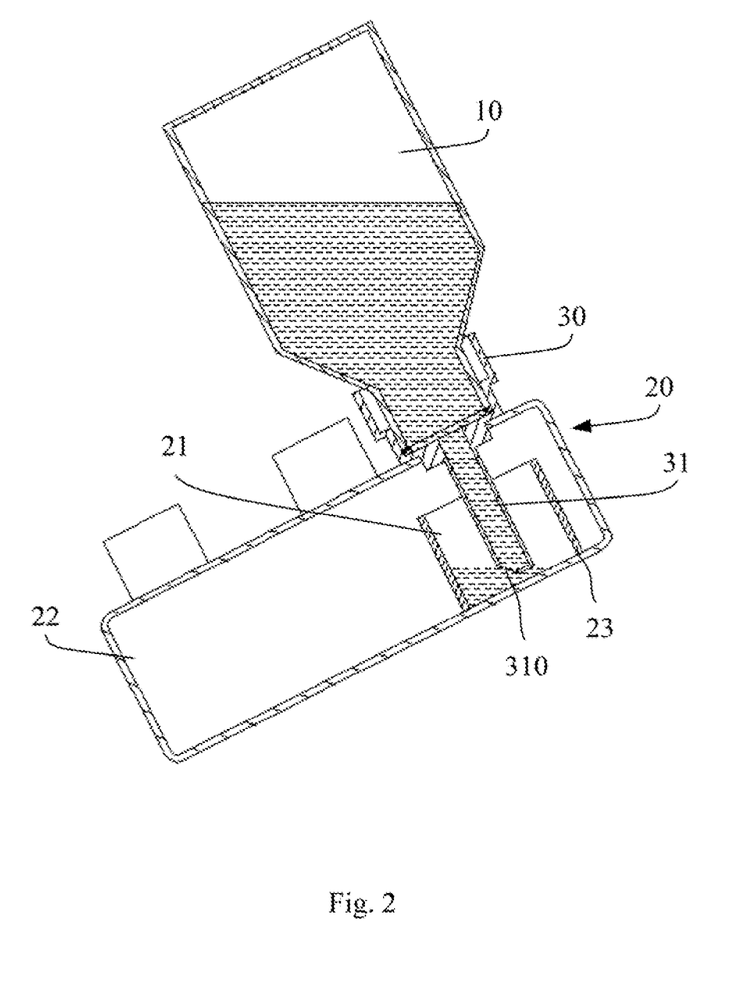
FIG. 2 and FIG. 3 are schematic diagrams of usage states in different sloping states according to the embodiment as shown in FIG. 1 of the present disclosure.

Under the condition as shown in FIG. 2, the humidification device tilts leftward, the water in the transition chamber 21 flows to a left bottom corner of the transition chamber 21 under the action of gravity, and the water in the accommodating chamber 22 flows to the left bottom corner of the accommodating chamber 22 under the action of gravity. When the water level of the transition chamber 21 is flush with the end portion opening 310 of the liquid inlet pipeline 31, the liquid storage portion 10 and the liquid inlet pipeline 31 may form a sealed environment to play a role in the liquid inlet pipeline 31 and prevent the water in the liquid storage portion 10 from further flowing into the transition chamber 21 via the liquid inlet pipeline 31. As long as the end portion opening 310 of the liquid inlet pipeline 31 is lower than the liquid level of the transition chamber 21, and the liquid storage portion 10 is in a sealed state, the liquid storage portion 10 does not supplement the water to the transition chamber 21 continuously. In this way, the water in the liquid storage portion 10 can be effectively prevented from largely entering the heating portion 20 when the humidification device is in the sloping state as shown in FIG. 2.

Figure 3:
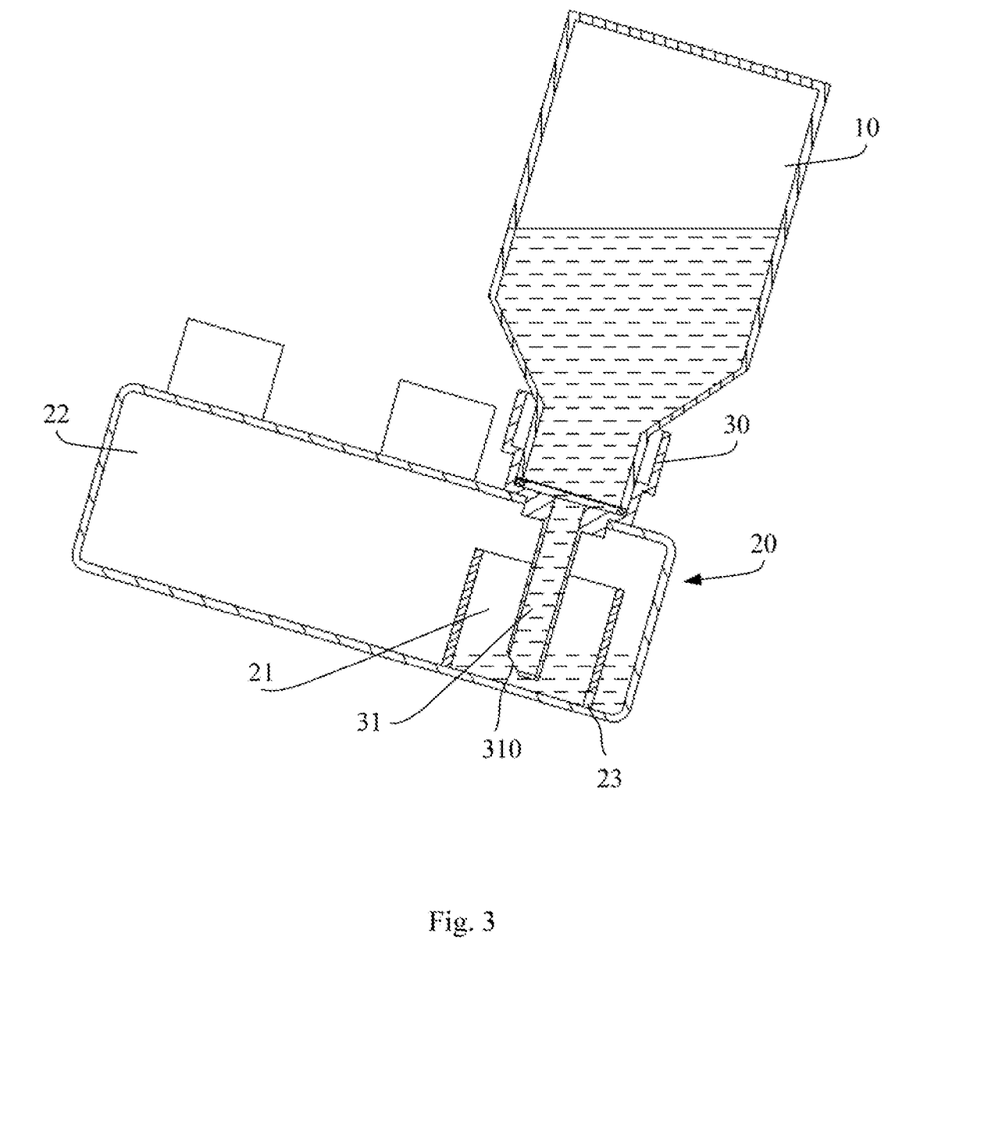

In the case as shown in FIG. 3, the humidification device tilts rightward, a distance between the water level of the transition chamber 21 and the communicating pore 23 becomes larger and larger, the water level of the transition chamber 21 may be above that of the accommodating chamber 22, and thus the water in the transition chamber 21 may flow into the accommodating chamber 22 under the action of gravity. Because the water flows to the communicating pore 23, when the water levels at the two sides of the communicating pore 23 are flush approximately, flow of water between the transition chamber 21 and the accommodating chamber 22 may become very slow, and thus the water in the liquid storage portion 10 does not flow to the transition chamber 21 continuously. In addition, the sectional area of the communicating pore 23 is very small, thus the water does not flow from the transition chamber 21 to the accommodating chamber 22 or flow from the accommodating chamber 22 to the transition chamber 21 quickly. When the transition chamber 21 is positioned next to a right edge position of the heating portion (the embodiment as shown in FIG. 1), space of the accommodating chamber 22 at a right side of the transition chamber 21 is relatively small. In this case, when the humidification device tilts rightward, the amount of the water flowing from the transition chamber 21 to the accommodating chamber 22 is also relatively small. This is because the water levels at the two sides of the communicating pore 23 are flush quickly in such a case.

It is to be noted that in the embodiment as shown in FIG. 1, the distance from the end portion opening 310, positioned in the transition chamber 21, of the liquid inlet pipeline 31 to the bottom of the transition chamber 21 determines a height from the water level of the transition chamber 21 to the bottom of the transition chamber 21.

In the embodiment as shown in FIG. 1, on the premise that the water in the liquid storage portion 10 does not quickly and largely flow into the heating portion 20, magnitude of inclined angle of the humidification device mainly depends on the height of the transition chamber 21. If the inclined angle of the humidification device is too large, the water in the transition area 21 flows out from the opening at an upward side of the transition area 21, and thus the water in the liquid storage portion 10 may quickly and largely flow into the heating portion 20.

In some other embodiments of the present disclosure, the transition chamber 21 and the accommodating chamber 22 in the heating portion 20 may be configured to communicate only through the communicating hole 23 while the rest portions are mutually isolated. Therefore, the water in the transition chamber 21 and the accommodating chamber 22 only can flow through the communicating hole 23, and the water in the transition chamber 21 can not enter the accommodating chamber 22 from other portions when the inclined angle of the humidification device is relatively large.

Figure 4:
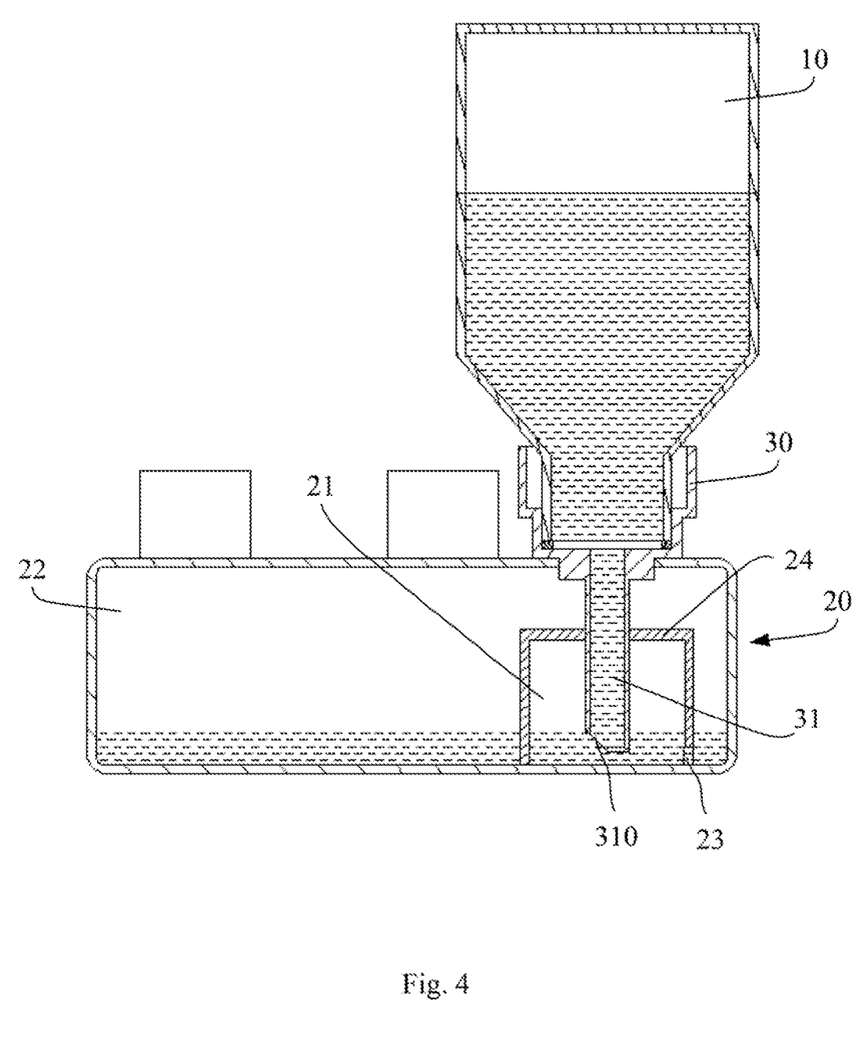
FIG. 4 is a schematic structural diagram of a humidification device according to another embodiment of the present disclosure.
Figure 5:
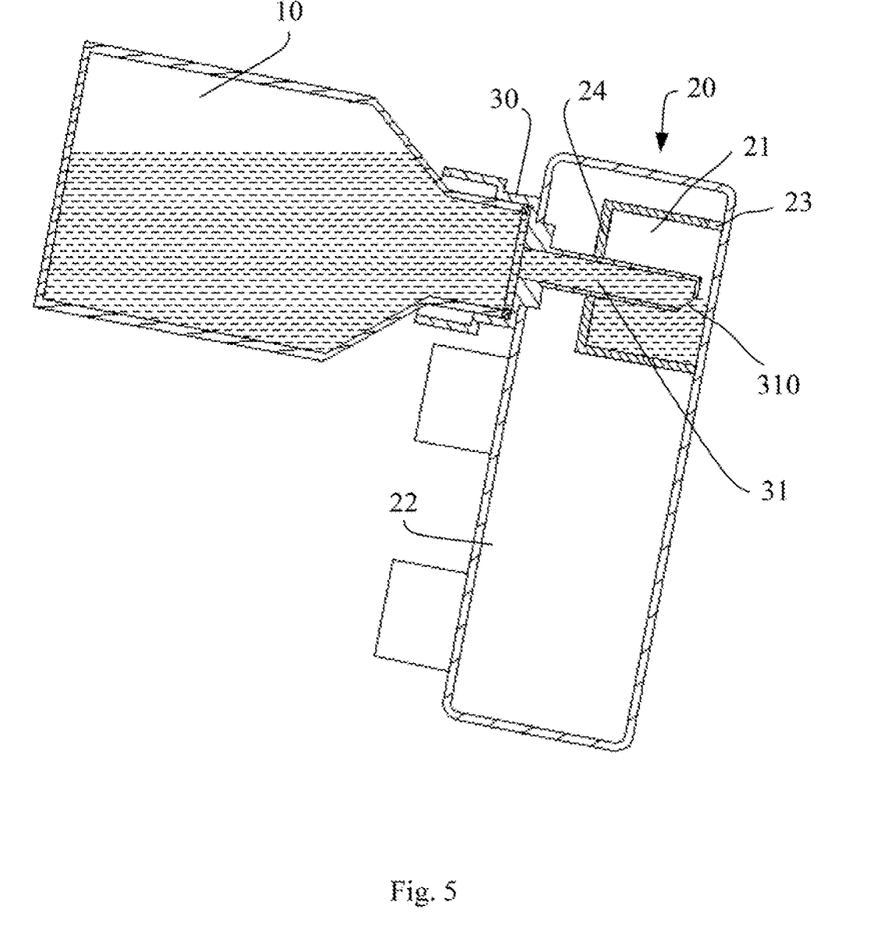
FIG. 5 and FIG. 6 are schematic diagrams of usage states in different sloping states according to the embodiment as shown in FIG. 4 of the present disclosure.
Figure 6:
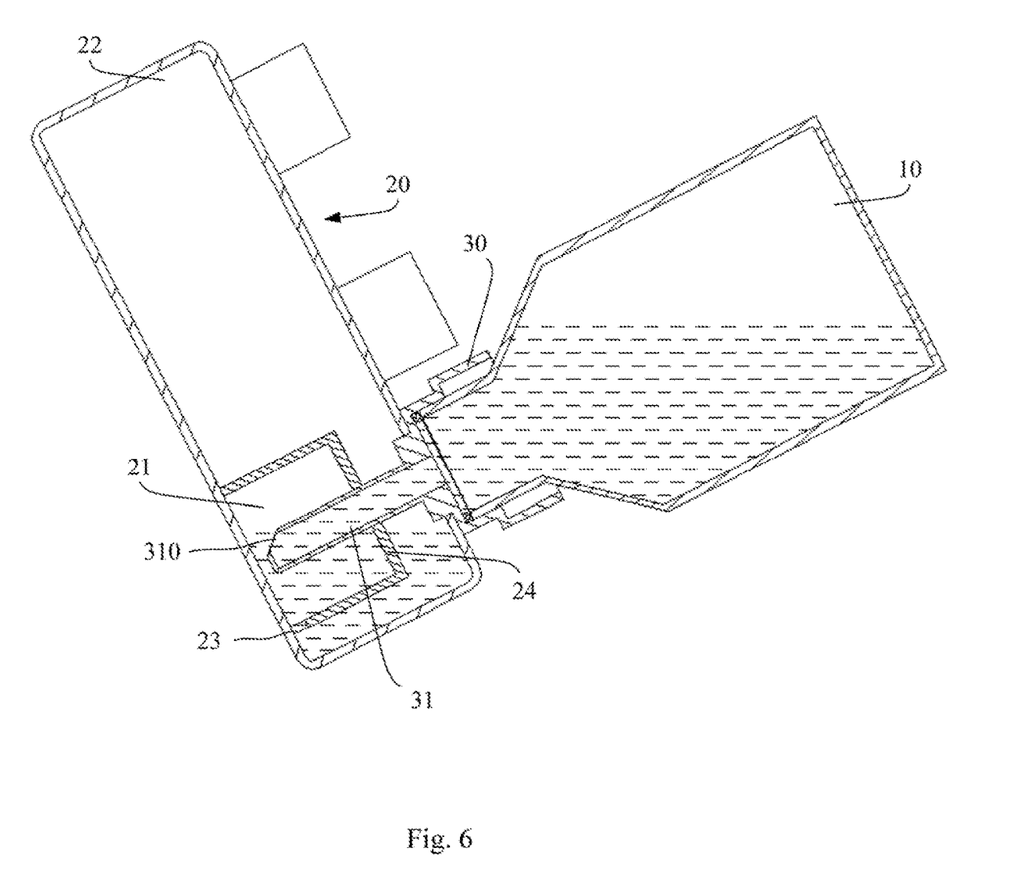

As shown in FIG. 4, in the humidification device according to the embodiment of the present disclosure, a top of the transition chamber 21 is provided with a top cover 24 for sealing the transition chamber 21. The liquid inlet pipeline 31 stretches into the transition chamber 21 through the top cover 24. When the transition chamber 21 is provided with the top cover 24, the water in the transition chamber 21 does not flow from the opening at the upward side of the transition chamber 21 to the accommodating chamber 22. As shown in FIG. 5 and FIG. 6, the inclined angle of the humidification device may be larger than that in the embodiment as shown in FIG. 1. Even though the water in the liquid storage portion 10 largely enters the transition chamber 21 at a relatively high speed via the liquid inlet pipeline 31, the water in the liquid storage portion 10 does not largely and quickly enter the accommodating chamber 22. In this way, occurrence of a case that the water in the liquid storage portion 10 largely enters the heating portion 20 to quickly reduce the water temperature of the heating portion 20, reduce the heating efficiency and prolong the heating time may be avoided, and too humid air may be not conveyed to the nasal cavity of the patient, thus avoiding making nasal discomfort of the patient or even choking water.

Figure 7:
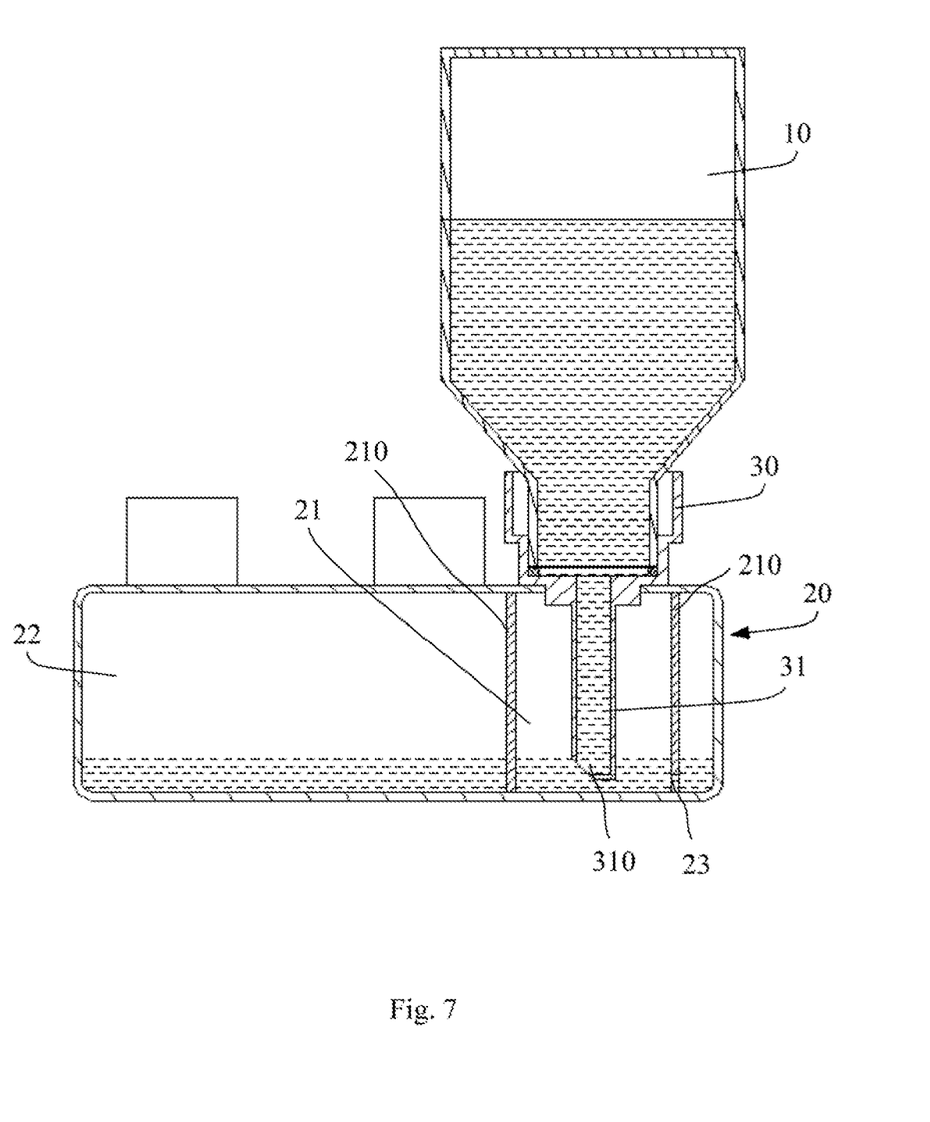
FIG. 7 is a schematic structural diagram of a humidification device according to still another embodiment of the present disclosure.

As shown in FIG. 7, a wall 210 of the transition chamber 21 also may directly extend upward to the top of the heating portion 20, and connect the top of the heating portion 20. Such a structure also may allow the transition chamber 21 to be communicated with the accommodating chamber 22 only through the communicating hole 23, so that the water in the transition chamber 21 and the accommodating chamber 22 flows only through the communicating hole 23. Therefore, no matter the inclined angle of the humidification device is large or small, even though the water in the transition chamber 21 and the accommodating chamber 22 may flow, the water only can flow at a very low speed through the communicating hole. Thus, even though the water in the liquid storage portion 10 largely enters the transition chamber 21 at a relatively high speed via the liquid inlet pipeline 31, the water in the liquid storage portion 10 does not largely and quickly enter the accommodating chamber 22. In this way, occurrence of a case that the water in the liquid storage portion 10 largely enters the heating portion 20 to quickly reduce the water temperature of the heating portion 20, reduce the heating efficiency and prolong the heating time may be avoided, and too humid air may be not conveyed to the nasal cavity of the patient, thus avoiding making nasal discomfort of the patient or even choking water.

Figure 8:
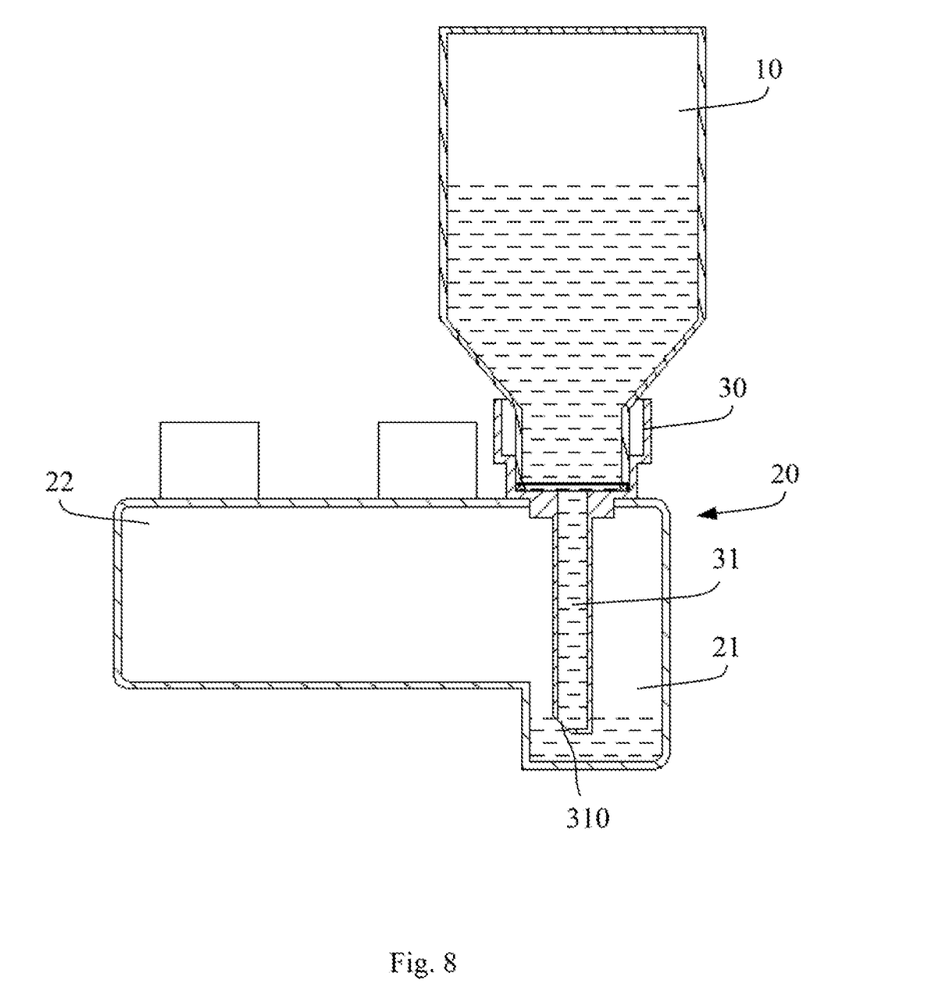
FIG. 8 is a schematic structural diagram of a humidification device according to still another embodiment of the present disclosure.

FIG. 8 is the humidification device according to another embodiment of the present disclosure.

As shown in FIG. 8, in the heating portion 20, a bottom surface of the transition chamber 21 is lower than that of the accommodating chamber 22, and the end portion opening 310 of the liquid inlet pipeline 31 is also lower than the bottom surface of the accommodating chamber 22. In some other embodiments, the bottom surface of the transition chamber 21 and the end portion opening 310 of the liquid inlet pipeline 31 may be somewhat lower than the bottom surface of the accommodating chamber 22. The water first enters and stays in the transition chamber 21 via the liquid inlet pipeline 31 and then is supplemented to the accommodating chamber 22 as needed. Such a setting may ensure that under a normal use condition, the water level of the transition chamber 21 is lower than the bottom surface of the accommodating chamber 22, so that when the water level of the transition chamber 21 is flush with the end portion opening 310 of the liquid inlet pipeline 31, the liquid inlet pipeline 31 may be sealed, thereby preventing the water in the liquid storage portion 10 from further flowing into the transition chamber 21 via the liquid inlet pipeline 31.

Figure 9:
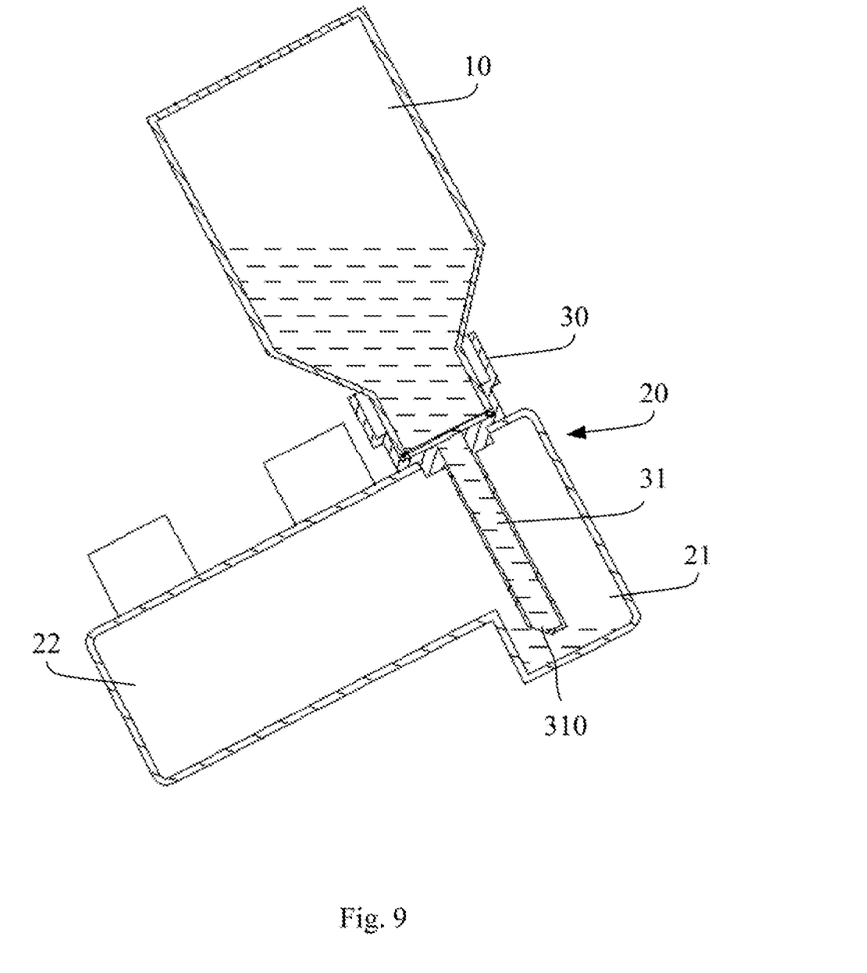
FIG. 9 and FIG. 10 are schematic diagrams of usage states in different sloping states according to the embodiment as shown in FIG. 8 of the present disclosure.
Figure 10:
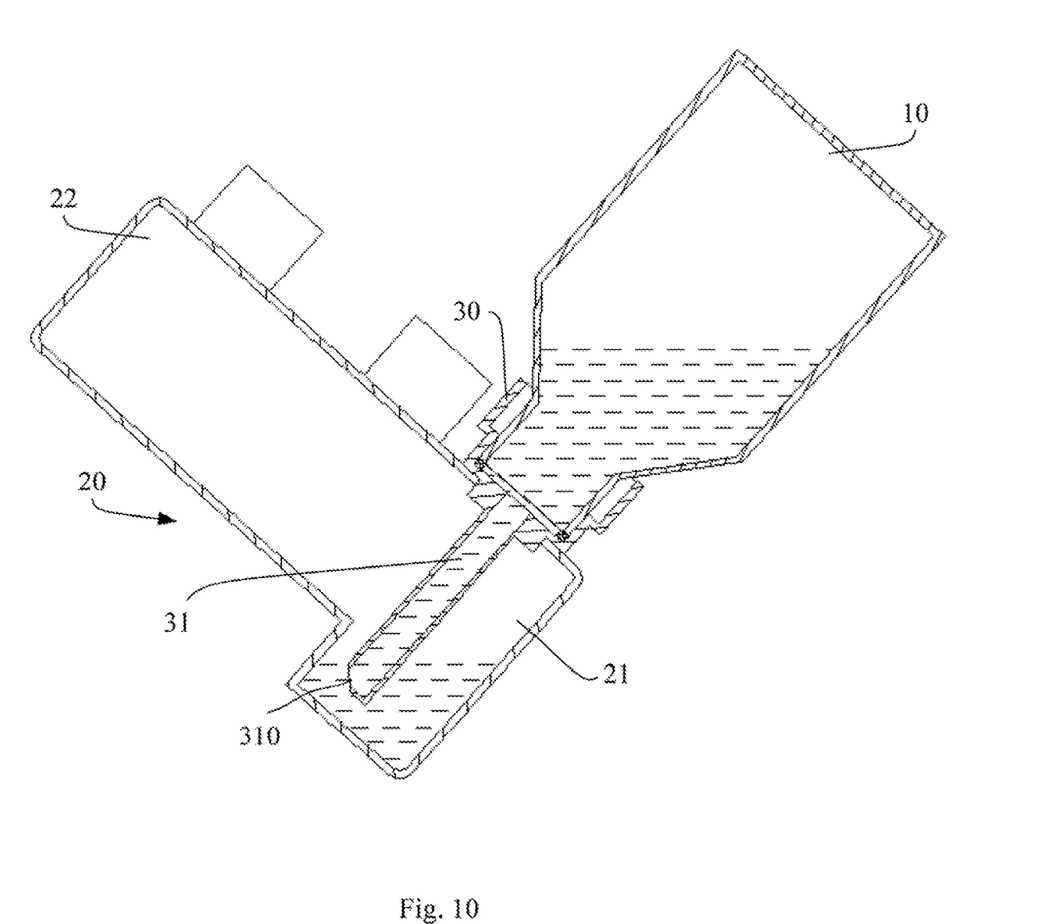

When the humidification device tilts as shown in FIG. 9 or FIG. 10, as long as the water level of the transition chamber 21 is not lower than the end portion opening 310 of the liquid inlet pipeline 31, the water in the liquid storage portion does not enter the heating portion 20. When a larger inclined angle causes that the water level of the transition chamber 21 is lower than the end portion opening 310 of the liquid inlet pipeline 31, the water in the liquid storage portion 10 may be supplemented to the transition chamber 21 in time, so that the water level in the transition chamber 21 is flush with the end portion opening 310 of the liquid inlet pipeline 31 again or above the end portion opening 310 of the liquid inlet pipeline 31.

In the above embodiment, the heating portion 20 further includes an air inlet and air outlet. Pressures of the air inlet and the air outlet are relatively constant, which ensured that air pressure in the heating portion 20 is relatively constant. In addition, it is to be noted that under a state that the pressures of the air inlet and the air outlet are constant, the liquid storage portion 10, the heating portion 20 and the liquid inlet structure 30 form into a sealing member, so that the liquid in the liquid inlet pipeline 31 stops flowing into the transition chamber 21 when the liquid level of the transition chamber 21 rises above the opening 310 of the liquid inlet pipeline 31 (the liquid level of the transition chamber 21 at least is flush with the opening 310 of the liquid inlet pipeline 31).

The humidifier according to the embodiments of the present disclosure mainly includes the above-mentioned humidification device and the heating element arranged at the bottom of the heating portion of the humidification device.

The ventilator according to the embodiments of the present disclosure mainly includes a main machine and the above-mentioned humidifier.

In the humidifier and the ventilator according to the embodiments of the present disclosure, a main improvement resides in the above-mentioned humidification device. To avoid unnecessary description, reference is made to the description of the embodiments of the foregoing humidification device for the humidifier and the ventilator of the present disclosure.

The embodiments of the present disclosure can effectively guarantee that a relatively large amount of water does not flow into the heating portion of the humidification device within a short time. Thus, a higher heating efficiency can be guaranteed, and occurrence of a case that more water is present in the heating portion so that the air entering the nasal cavity of the patient is too humid or even the water is brought to the nasal cavity of the patient can be avoided.

The above are embodiments disclosed by the present disclosure. However, the described contents are merely embodiments adopted for better understanding the technical solutions of the present disclosure rather than limiting the present disclosure. Any person skilled in the art can make any modification and variation to the implementing forms or details without departing from the spirit and scope of the present disclosure. However, the patent protection scope of the present disclosure should still be subjected to the scope defined in the appended claims.

What is claimed is:

1. A humidification device, comprising a heating portion and a liquid inlet structure adding liquid to the heating portion, wherein the heating portion comprises an accommodating chamber and a transition chamber limiting the amount of liquid in the accommodating chamber, the transition chamber has a pair of opposite walls, at least one of the opposite walls has a top and a bottom that are contiguous, respectively, with a top and a bottom of the accommodating chamber, and the liquid inlet structure is communicated with the transition chamber and allows the liquid to enter the transition chamber, the liquid inlet structure has an open top, a bottom and a wall connecting the top and the bottom;

a liquid storage portion to store liquid entering the transition chamber, the liquid storage portion has an open bottom that is contiguous with the bottom of the liquid inlet structure;

the liquid inlet structure comprises a liquid inlet pipeline, the liquid inlet pipeline extends into the transition chamber, and a reserved interval is provided between an opening of the liquid inlet pipeline and a bottom of the transition chamber;

a communicating pore is provided between the transition chamber and the accommodating chamber.

2. The humidification device according to claim 1, wherein a sectional area of the communicating pore is smaller than that of the opening of the liquid inlet pipeline.

3. The humidification device according to claim 2, wherein the communicating pore is different, in orientation, from the opening of the liquid inlet pipeline.

4. The humidification device according to claim 1, wherein a top of the transition chamber is provided with a top cover or a wall of the transition chamber extends to a top of the heating portion.

5. The humidification device according to claim 1, wherein a volume of the transition chamber is smaller than that of the accommodating chamber.

6. The humidification device according to claim 1, wherein the liquid inlet pipeline is located in an edge position of the accommodating chamber, and the opening of the liquid inlet pipeline is close to a side wall of the accommodating chamber and is back to the side wall.

7. The humidification device according to claim 1, wherein the reserved interval is greater than 5 mm and smaller than 30 mm.

8. The humidification device according to claim 1, wherein the connection between the heating portion and the liquid inlet structure is a detachable connection.

9. A humidifier, comprising a heating element and a humidification device wherein the humidification device comprises a heating portion and a liquid inlet structure adding liquid to the heating portion, the heating portion comprises an accommodating chamber and a transition chamber limiting the amount of liquid in the accommodating chamber, the transition chamber has a pair of opposite walls, at least one of the opposite walls has a top and a bottom that are contiguous, respectively, with a top and a bottom of the accommodating chamber, and the liquid inlet structure is communicated with the transition chamber and allows the liquid to enter the transition chamber, the liquid inlet structure has an open top, a bottom and a wall connecting the top and the bottom;
- a liquid storage portion to store liquid entering the transition chamber, the liquid storage portion has an open bottom that is contiguous with the bottom of the liquid inlet structure; and
- wherein the heating element heats liquid in the heating portion;
- the liquid inlet structure comprises a liquid inlet pipeline, the liquid inlet pipeline extends into the transition chamber, and a reserved interval is provided between an opening of the liquid inlet pipeline and a bottom of the transition chamber;
- a communicating pore is provided between the transition chamber and the accommodating chamber.

10. The humidifier according to claim 9, wherein a sectional area of the communicating pore is smaller than that of the opening of the liquid inlet pipeline.

11. The humidifier according to claim 9, wherein a top of the transition chamber is provided with a top cover or a wall of the transition chamber extends to a top of the heating portion.

12. A ventilator, comprising a main machine and a humidifier connected with the main machine, wherein the humidifier comprises a heating element and a humidification device, the humidification device comprises a heating portion and a liquid inlet structure adding liquid to the heating portion, the heating portion comprises an accommodating chamber and a transition chamber limiting the amount of liquid in the accommodating chamber, the transition chamber has a pair of opposite walls, at least one of the opposite walls has a top and a bottom that are contiguous, respectively, with a top and a bottom of the accommodating chamber, the liquid inlet structure is communicated with the transition chamber and allows the liquid to enter the transition chamber, the liquid inlet structure has an open top, a bottom and a wall connecting the top and the bottom;
- a liquid storage portion to store liquid entering the transition chamber, the liquid storage portion has an open bottom that is contiguous with the bottom of the liquid inlet structure, and the heating element heats liquid in the heating portion;
- the liquid inlet structure comprises a liquid inlet pipeline, the liquid inlet pipeline extends into the transition chamber, and a reserved interval is provided between an opening of the liquid inlet pipeline and a bottom of the transition chamber;
- a communicating pore is provided between the transition chamber and the accommodating chamber.

13. The ventilator according to claim 12, wherein a sectional area of the communicating pore is smaller than that of the opening of the liquid inlet pipeline.

* * * * *